(12) United States Patent
Mentink et al.

(10) Patent No.: US 11,806,413 B2
(45) Date of Patent: Nov. 7, 2023

(54) EMULSIFYING COMPOSITION FOR COSMETIC USE FOR PRODUCING AN O/W PICKERING EMULSION AND PROCESS FOR PRODUCING THIS EMULSION

(71) Applicant: ROQUETTE FRERES, Lestrem (FR)

(72) Inventors: Léon Mentink, Lille (FR); Daniel Wils, Morbecque (FR); Anne-Marie Lheritier, Cergy (FR); Sophie Piot, Paris (FR); Marc Lavarde, Cergy (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 17/047,587

(22) PCT Filed: Apr. 16, 2019

(86) PCT No.: PCT/FR2019/050896
§ 371 (c)(1),
(2) Date: Oct. 14, 2020

(87) PCT Pub. No.: WO2019/202255
PCT Pub. Date: Oct. 24, 2019

(65) Prior Publication Data
US 2021/0113438 A1 Apr. 22, 2021

(30) Foreign Application Priority Data

Apr. 17, 2018 (FR) .................................... 18 53362

(51) Int. Cl.
| | |
|---|---|
| *A61K 8/06* | (2006.01) |
| *A61K 8/34* | (2006.01) |
| *A61K 8/73* | (2006.01) |
| *A61K 8/92* | (2006.01) |
| *A61Q 19/00* | (2006.01) |

(52) U.S. Cl.
CPC .............. *A61K 8/062* (2013.01); *A61K 8/342* (2013.01); *A61K 8/345* (2013.01); *A61K 8/731* (2013.01); *A61K 8/738* (2013.01); *A61K 8/922* (2013.01); *A61Q 19/00* (2013.01); *A61K 2800/10* (2013.01); *A61K 2800/412* (2013.01); *A61K 2800/48* (2013.01); *A61K 2800/52* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 5,607,664 A | 3/1997 | Oreal | |
| 5,665,687 A * | 9/1997 | Khayat | A61K 8/0241 510/159 |
| 5,976,555 A * | 11/1999 | Liu | A61Q 19/00 424/59 |
| 2010/0075403 A1* | 3/2010 | Takano | C12N 1/18 435/255.2 |
| 2016/0051459 A1* | 2/2016 | Perassinoto | A61K 8/062 424/59 |

FOREIGN PATENT DOCUMENTS

| | | |
|---|---|---|
| CN | 107982096 A | 5/2018 |
| DE | 10239647 A1 | 3/2004 |
| EP | 3037082 A1 | 6/2016 |
| EP | 3037083 A1 | 6/2016 |
| FR | 2823438 A1 | 10/2002 |
| FR | 2858777 A1 | 2/2005 |
| WO | 2008003685 A1 | 1/2008 |

OTHER PUBLICATIONS

The Written Opinion of the International Searching Authority, dated Nov. 25, 2019, in the corresponding PCT Appl. No. PCT/FR2019/050896 (Year: 2019).*
Seppic, Montanov 68 Safety Data Sheet, Mar. 26, 2020 (Year: 2020).*
Poulson et al., Cyclodextrins: Structural, Chemical, and Physical Properties, and Applications, Polysaccharides 2022, 3, 1-31. https://doi.org/10.3390/polysaccharides3010001 (Year: 2022).*
The English translation of the International Search Report, dated Nov. 25, 2019, in the corresponding PCT Appl. No. PCT/FR2019/050896.
Product information, "Energize Razor," by Wilkinson Sword, published on Jan. 2018.
Marto et al., "Pickering emulsions: challenges and opportunities in topical delivery," Expert Opinion on Drug Delivery, Published online on May 11, 2016.
Product information, "CC Cream SPF 40," by purminerals, published on Jul. 2013.
Product information, "Brightening Solution Ultra Fine Microfiber Brightening Sheet Mask," by Have & Be, published on Mar. 2018.
Rayner et al., "Quinoa starch granules as stabilizing particles for production of Pickering emulsions," Faraday Discuss., 2012, 158, pp. 139-155.

* cited by examiner

*Primary Examiner* — Jennifer A Berrios

(57) ABSTRACT

The application relates to an emulsifying composition, in particular for cosmetic use, allowing an oil-in-water emulsion (O/W) to be obtained, the emulsion comprising at least one cyclodextrin and at least one O/W emulsifier of natural origin with a hydrophilic-lipophilic balance value (HLB) of more than 8. The O/W emulsifier of natural origin can be selected from alkyl polyglucosides, mixtures of at least one alkyl polyglucoside and at least one fatty alcohol, and non-ethoxylated polyol fatty esters. The application also relates to a composition of the Pickering emulsion type, in particular for cosmetic use, containing the emulsifying composition according to the invention, and to the process for preparing such a composition of the O/W Pickering emulsion type, in particular at low temperatures.

15 Claims, 1 Drawing Sheet

EMULSIFYING COMPOSITION FOR COSMETIC USE FOR PRODUCING AN O/W PICKERING EMULSION AND PROCESS FOR PRODUCING THIS EMULSION

CROSS-REFERENCE TO RELATED APPLICATIONS

This application is a National Stage Application of PCT/FR2019/050896 filed Apr. 16, 2019, which claims priority from French Patent Application No. 18 53362, filed on Apr. 17, 2018. The priority of said PCT and French Patent Application are claimed. Each of the prior mentioned applications is hereby incorporated by reference herein in its entirety.

The present invention relates to an emulsifying composition of plant origin which is ready to use and is directly utilizable cold, and which finds application especially in the field of cosmetic compositions. This composition is sufficient by itself and allows the direct stabilization of an emulsion without the need to add a co-emulsifier of petrochemical origin. More particularly, this emulsifying composition enables the easy production of very fine O/W emulsions with varied textures, which are highly compatible with the skin and which, moreover, exhibit a dry and fresh, silky, and nongreasy feel even when the fatty phase content of the emulsion is high. This composition also makes it possible to advantageously reduce the amount of emulsifier of natural origin required to obtain an O/W emulsion.

An emulsion is a dispersion of a liquid (or of a substance which has been rendered liquid) as fine droplets in another liquid, this liquid being immiscible with the first. It exhibits a macroscopically homogeneous appearance, yet appears homogeneous under the microscope. The liquid in droplet form is called the disperse (or discontinuous) phase, whereas the other liquid is called the dispersing (or continuous) phase. In general, an emulsion is composed of water and oil and of two phases (simple emulsion): a hydrophilic (aqueous) phase and a lipophilic (fatty) phase. The emulsions most commonly encountered are emulsions which comprise a lipophilic phase dispersed in a continuous aqueous phase, and are referred to as oil-in-water (O/W) emulsions, as opposed to water-in-oil (O/W) emulsions.

Many cosmetic compositions are emulsions, typically simple emulsions, which are stabilized by surfactants, also called emulsifiers. As an example, document EP 0 685 227 proposes a very complex system of cosmetic antisun compositions, comprising an aqueous continuous phase, a protective system capable of screening out UV rays, a surfactant, organic solvents (lower polyols and alcohols), and at least one polymer or, more particularly, a crosslinked copolymer (alkyl acrylates, vinyl acetate).

Document FR 2 858 777, in turn, describes an oil-in-water emulsion containing at least one fatty substance (fatty acid esters, waxes, butters, natural oils—of plant, animal or marine origin—or synthetic or mineral oils, hydrogenated oils, and mixtures thereof), at least one surfactant (ethoxylated fatty acid esters of polyglycerol, alcohol ethoxylates), at least one co-surfactant, and water.

Document DE 102 39 647 A1, for its part, describes cosmetic and/or dermatological oil/water (O/W) emulsions containing (a) an aqueous phase, (b) an oily phase of 0.5 to 10% by weight of non-polar to moderately polar oil(s) with a polarity of 20-60 mN/m, (c) 0.005 to 10% by weight of cyclodextrin derivative(s) and optionally other cosmetic and/or dermatological agents, adjuvants and additives.

Document EP 3 037 083 A1, for its part, describes a sun protection composition without emulsifier.

Document FR 2 823 438 A1, for its part, describes an oil-in-water emulsion, based on a self-emulsifying combination of fatty alcohols and glucolipids in a weight ratio of between 10:1 and 4:1, and it stands out in that it also comprises a viscosifying agent in the fatty phase.

However, the use of surfactants in products intended for application to humans or animals, whether in topical, oral or another form, may be problematic. The reason is that the surfactants may damage the cell membranes. Thus, especially in the cosmetics field, efforts to reduce the potentially harmful effects of surfactants, or even to eliminate recourse to surfactants, have been authorized.

Thus, one of the aims of the present invention is to provide an emulsifying composition which is able to form a stable emulsion by adding oil or fatty substance when placed in the presence of water, in particular according to a process referred to as a "cold process".

Advantageously, this emulsifying composition according to the invention makes it possible to significantly reduce the use of surfactants that are of petrochemical origin and are non-biodegradable, in particular glycol derivatives and ethoxylated or polyethoxylated derivatives. According to another variant, it makes it possible to eliminate the need for these surfactants of petrochemical origin.

From this standpoint, the composition of the present invention also enables the production of Pickering emulsions. Emulsions of this type are devoid of surfactant and are stabilized by colloidal particles such as, typically, silicas, which take up position at the interfaces of the continuous phase and the disperse phase. In the context of the present invention, these colloidal particles are organic particles consisting of inclusion complexes of at least one cyclodextrin with at least one fatty molecule. These particles have very advantageous compatibility with the skin or the hair, and do not damage animal cell membranes.

This result is all the more noteworthy for the fact that in the prior art, it has been shown that the production of emulsifying systems for cosmetic use, containing cyclodextrins, does not make it possible to obtain emulsions easily and directly under cold conditions: it was hitherto necessary to have recourse to conventional surfactants that work at high temperature and are generally of petrochemical origin. This is the teaching especially of document EP 2 091 502 B1, which describes an O/W emulsion containing water, a fatty substance, a modified polysaccharide, and a cyclodextrin, with the essential feature of this O/W emulsion being that it contains surfactants with a molecular weight of less than 5000 g/mol in an amount of less than 2% by weight. It was therefore neither known nor obvious to produce emulsifying systems containing cyclodextrins that produce very fine and very stable emulsions without having recourse to ordinary surfactants of petrochemical origin.

Another object of the present invention is to provide a composition of natural origin. The natural origin of the ingredients used to formulate products of everyday use such as cosmetic compositions is nowadays a major issue, in relation not only to the safeguarding and protection of our environment but also to the well-being of consumers. In this regard, the composition of the present invention makes it possible to reduce, or even replace conventional emulsifiers, especially ethoxylated emulsifiers, which it is nowadays desirable to replace for environmental issues (poor biodegradability) and safety (ethylene oxide is toxic and flammable).

Another object of the present invention is to provide a ready-to-use emulsifying composition which the formulator can employ very simply, with minimum input of energy, especially by introduction of all of the ingredients into a single vessel or reactor (a so-called "one pot" formulation). From the standpoint of its use, the composition to which the present invention relates is advantageously utilizable according to "a cold process", in other words even at ambient temperature, in contrast to many solid or pastelike conventional emulsifiers, such as waxes, the use of which requires an increase in the temperature (an ingredient which needs to be melted and is utilizable "hot"). The notion of cold process includes emulsification processes in which the only heat input is that due to the energy dissipation caused by mechanical stirring. By "cold process" is meant that the emulsifying composition can be used directly by dispersion in water at a water temperature of less than 45° C., better still less than 35° C., and even better still at ambient temperature.

Another object of the present invention is to provide an emulsifying composition for broad-spectrum cosmetic use, meaning that it is versatile in terms of the final products envisioned: from this standpoint, the composition according to the invention may be used in products as diverse as lotions, creams, gels, milks, etc. Moreover, said composition is advantageously nonirritant and nonallergic for the skin. It offers the advantage, furthermore, of not being dependent on pH or on the presence of electrolytes: in other words, its emulsifying capacity is unaffected by the pH of the medium or by the presence of mono-, di- or trivalent salts. This criterion is all the more important since, in general, products for cosmetic use and notably for topical application are liable to be subjected or exposed to pH variations (by way of example, the pH of the skin is slightly acidic, and ranges between 4 and 6). Having a product which does not have any particular limit for use in terms of pH thus represents a very great technical advantage for a cosmetic composition.

Lastly, another object of the present invention is to provide a composition for cosmetic use that offers a broad range of sensorial properties of interest, such as, in particular, a sensation of freshness on the skin, or an unctuous texture. Specifically, the emulsifying composition of the invention allows the easy production of O/W emulsions that are both stable and very fine and which have tailorable textures and exhibit a fresh, silky and nongreasy feel, even where the contents of disperse fatty phase are high. It is thus possible to obtain emulsions that have a good emollient effect on the skin and also a good moisturizing effect on the upper layers of the epidermis.

The entirety of these objectives, constituting a complex technical problem to be solved, is ultimately achieved by virtue of the principal subject of the present invention, this being an emulsifying composition, especially for cosmetic use, which enables the production of an oil-in-water (O/W) emulsion, comprising:
1) at least one cyclodextrin,
2) and at least one O/W emulsifier of natural origin,
the O/W emulsifier having a hydrophilic-lipophilic balance (HLB) greater than 8, preferentially greater than or equal to 9.

The calculation of the HLB takes account of the molecular masses of the hydrophilic portions and the molecular mass of the molecule in question, and can be obtained according to the following equation:

$$HLB = 20 \frac{\text{Molecular mass of hydrophilic portion}}{\text{Molecular mass of the molecule}}$$

In the present application, the term "cyclodextrin" denotes and includes any cyclodextrins otherwise known, such as unsubstituted native cyclodextrins containing from 6 to 12 glucose units bonded by covalent bonds between carbons 1 and 4, and especially alpha-, beta- and gamma-cyclodextrins containing respectively 6, 7 and 8 glucose units.

This term likewise covers "cyclodextrin derivatives", these being molecules in which at least some of the hydroxyl groups OH have been converted into groups OR, where R denotes, generally, an alkyl group. From this standpoint, the cyclodextrin derivatives include, in particular, methylated and ethylated cyclodextrins, but also those substituted with a hydroxyalkyl group, such as hydroxypropylated and hydroxyethylated cyclodextrins.

The preferred cyclodextrins according to the present invention are alpha-, beta- and gamma-cyclodextrins, with native beta-cyclodextrin being most preferred.

The cyclodextrin may in particular take the form of a crystalline, pseudocrystalline or amorphous powder.

In the present application, the term "O/W emulsifier of natural origin" denotes any molecule obtained from renewable resources, especially one extracted from or secreted by plants, microorganisms or algae and enabling, after physical, chemical or enzymatic modification, the production of a water-in-oil O/W emulsion, or of promoting the stability of such an emulsion. Also included under this definition are therefore products called O/W co-emulsifiers of natural origin.

The applicant has been able to observe, after numerous tests and experimental designs, that quite surprisingly and unexpectedly, the combination, with a cyclodextrin, of an emulsifier of natural origin having a hydrophilic-lipophilic balance (HLB) greater than 8, preferentially greater than or equal to 9, making it possible in a manner known per se to obtain an O/W emulsion, far from having negative consequences on the stability and the quality of O/W emulsions, on the contrary has a very favorable effect. It is thus advantageously possible to reduce the amount of emulsifier of natural origin required to obtain a satisfactory and stable emulsion, and, moreover, to finely adjust the texture and the sensory profile of the emulsion.

Without wishing to be tied to any particular theory, it appears that the presence of very small amounts of an O/W emulsifier of natural origin greatly facilitates the formation in situ of inclusion complexes between the cyclodextrin and certain specific molecules present in the disperse fatty phase, and in the form of colloidal, solid or semiliquid particles, which take up position at the oil and water interfaces. These particles are very compatible physically and sensorially with the skin or the hair, and do not damage animal cell membranes.

It has been shown that the combination of cyclodextrin with small amounts of an O/W emulsifier of natural origin having a hydrophilic-lipophilic balance (HLB) greater than 8, preferentially greater than or equal to 9, makes it possible to obtain very stable emulsions with drops less than 30 µm in size, or even less than 10 µm in size. It has also been shown that this addition allows the ultimate viscosity of the O/W emulsion to be adjusted. By virtue of this adjustment of the viscosity, combined with the droplet size of less than 30 µm, or even 10 µm, the texture of the emulsions can be advantageously adjusted.

The O/W emulsifier of natural origin, which has a hydrophilic-lipophilic balance (HLB) of greater than 8, preferentially greater than or equal to 9, is preferably present in the emulsifying composition in a ratio of between 0.01 and 1 part, preferably between 0.05 and 0.5 part, more preferentially between 0.10 and 0.35 part, and even better still between 0.15 and 0.30 part per 1 part by weight of cyclodextrin.

This O/W emulsifier of natural origin may also be selected from products which are naturally biodegradable in hydrated natural medium, especially with a hydrophilic-lipophilic balance (HLB) of between 8 and 20, preferably between 9 and 16, even better still between 11 and 14.

As an example, this O/W emulsifier of natural origin may be selected from the following products, provided they meet the above condition relating to the HLB: alkyl polyglucosides; mixtures of at least one alkyl poly glucoside and at least one fatty alcohol; nonethoxylated fatty esters of polyols, and especially from nonethoxylated fatty esters of glycerol, polyglycerols, sorbitol, sorbitan, anhydrohexitols such as, more particularly, isosorbide, of mannitol, of xylitol, of erythritol, of maltitol, of sucrose, of glucose, of polydextrose, of hydrogenated glucose syrups, of dextrins, and of hydrolyzed starches.

The O/W emulsifier of natural origin is preferably selected to be naturally biodegradable in a hydrated natural environment. It may especially comprise nonethoxylated fatty esters of polyols obtained from fatty acid or by transesterification from an oil or mixtures of oils. The fatty acids used comprise from 8 to 22 carbon atoms, preferably from 10 to 18 carbon atoms, and more particularly from 12 to 18 carbon atoms. These acids may be linear or branched, saturated or unsaturated, and may possess one or more pendent hydroxyl functions. The oils may be saturated or unsaturated, from liquid to solid at ambient temperature, and may optionally possess hydroxyl functions, preferably with an iodine index of between 1 and 145, and more particularly from 5 to 105.

The O/W emulsifier of natural origin may more particularly be selected from polyglycerol esters and preferably from esters obtained from the reaction of polyglycerols comprising from 2 to 12 glycerol units, preferably from 3 to 10 glycerol units, with at least one unhydrogenated or partially hydrogenated plant oil with an iodine index of between 1 and 15, and more particularly from 5 to 10. They may in particular be oleic, stearic, palmitic, lauric, diisostearic and caprylic esters of polyglycerols and in particular the following products: Polyglyceryl-5 Dioleate with an HLB of approximately 8 (such as Dermofeel® G 5 DO from Evonik Dr. Straetmans GmbH), Polyglyceryl-2 Caprate with an HLB of approximately 9 (such as Hydriol® PGC.2 from Hydrior), Polyglyceryl-3 Stearate with an HLB of approximately 9 (such as Dermofeel® PS from Evonik Dr. Straetmans GmbH), Polyglyceryl-2 Laurate with an HLB of approximately 9 (such as Dermofeel® G2L from Evonik Dr. Straetmans GmbH), Polyglyceryl-3 Palmitate with an HLB of approximately 10 (such as Dermofeel® PP from Evonik Dr. Straetmans GmbH), Polyglyceryl-10 Diisostearate with an HLB of approximately 11 (such as Dermofeel® G10 DI from Evonik Dr. Straetmans GmbH), Polyglyceryl-6 Caprylate with an HLB of approximately 11.5, Polyglyceryl-5 Laurate with an HLB of approximately 13 (such as Dermofeel® G5L from Evonik Dr. Straetmans GmbH), Polyglyceryl-3 Caprate with an HLB of approximately 14 (such as Hydriol® PGC.3 from Hydrior), Polyglyceryl-4 Caprate with an HLB of approximately 14 (such as Massocare PG4 C from Masso), Polyglyceryl-10 Monolaurate with an HLB of approximately 14.8, Polyglyceryl-6 Caprylate with an HLB of approximately 15 (such as Dermofeel® G 6 CY from Dr. Straetmans GmbH/Evonik), Polyglyceryl-10 Laurate with an HLB of approximately 16 (such as Dermofeel® G 10 L from Dr. Straetmans GmbH/Evonik).

The O/W emulsifier of natural origin is preferably selected from alkyl polyglucosides, sometimes also called alkyl polyglycosides, and designated by the acronym APGs. These emulsifiers are nonionic surfactants that are well known per se. Patent FR 2 948 285 gives a presentation of them in terms of structure, and explains how to prepare them. They can be represented by the following general formula (I): $R_1$—O—$(R_2$—O$)_p$—$(S)_n$
wherein:
S represents a reducing saccharide, which may comprise between 5 and 6 carbon atoms,
R1 denotes a linear or branched alkyl and/or alkenyl radical comprising approximately 8 to 24 carbon atoms, or an alkylphenyl radical of which the linear or branched alkyl group comprises approximately 8 to 24 carbon atoms,
R2 denotes an alkylene radical comprising from 2 to 4 carbon atoms,
n denotes a value ranging from 1 to 15,
p denotes a value ranging from 0 to 10.

The term "reducing saccharide" denotes, in formula (I), the saccharide derivatives which do not exhibit in their structures a glycosidic bond established between an anomeric carbon and the oxygen of an acetal group as defined in the reference manual: Biochemistry, Daniel Voet/Judith G. Voet, p. 250, John Wyley & Sons, 1990. The oligomeric structure $(S)_n$ can be in any form of isomerism, whether it is optical isomerism, geometric isomerism or positional isomerism; it can also represent a mixture of isomers.

According to one particular aspect of the present invention, in the definition of the compounds of formula (I), S represents a reducing saccharide selected from glucose, dextrose, sucrose, fructose, idose, gulose, galactose, maltose, isomaltose, maltotriose, lactose, cellobiose, mannose, ribose, xylose, arabinose, lyxose, allose, altrose, dextran or tallose and more particularly a reducing saccharide selected from glucose, xylose or arabinose.

A first preferred variant of alkyl polyglucosides according to the present invention are $C_{12}$-$C_{20}$ alkyl glucosides, that is to say the compounds of formula (I) wherein:
R1 more particularly denotes a linear or branched alkyl and/or alkenyl radical comprising approximately 12 to 20 carbon atoms,
p takes a value ranging from 0 to 3, and preferentially equal to zero,
S denotes glucose, fructose or galactose, and more preferentially glucose.

A second preferred variant of alkyl polyglucosides according to the present invention are the $C_{12}$-$C_{20}$ alkyl glucosides of the first preferred variant, wherein:
R1 more particularly denotes a linear alkyl radical comprising approximately from 12 to 20 carbon atoms,
p is equal to zero,
S stands for glucose.

Alkyl polyglucosides of formula (I) are in particular commercially available under the names: Plantacare® 810 UP ($R_1$ is $C_8$-$C_{10}$/INCI: caprylyl/capryl glucoside), Plantacare® 818 UP ($R_1$ is $C_8$-$C_{16}$ INCI: Coco-glucoside), Plantacare® 2000 UP ($R_1$ is $C_8$-$C_{16}$/INCI: decyl glucoside) and Plantacare® 1200 UP ($R_1$ is $C_{12}$-$C_{16}$/INCI: lauryl glucoside) sold by the company BASF; Macanol® 810 ($R_1$ is $C_8$-$C_{10}$), Macanol® 1200 ($R_1$ is $C_{12}$-$C_{14}$), Macanol® 816 (mixture of $R_1$ being $C_8$, $C_{10}$, $C_{12}$, $C_{14}$, $C_{16}$) sold by the company FCI Technology; Neocare MF 0718 ($R_1$ is $C_8$-$C_{10}$/INCI: caprylyl/capryl glucoside), Neocare MF 0012 ($R_1$ is $C_{12}$-$C_{14}$/

INCI: lauryl glucoside), Neocare MF 0002 ($R_1$ is $C_8$-$C_{16}$/INCI: decyl glucoside), Neocare MF 818 ($R_1$ is $C_8$-$C_{16}$/INCI: coco glucoside) sold by the company Neochem; Tego Care CG 90 ($R_1$ is $C_{14}$-$C_{16}$/INCI: cetearyl glucoside) sold by the company Evonik Healthcare.

The O/W emulsifier of natural origin can be a mixture consisting of at least one alkyl polyglucoside and at least one fatty alcohol. In these mixtures, the alkyl polyglucosides can be selected from all the alkyl polyglucosides of use in the invention, that have been described above. Linear or branched fatty alcohols having a total number of carbon atoms ranging from 8 to 24 can be used as fatty alcohols of use for mixing with the alkyl glucosides.

Mixtures of alkyl glucosides and fatty alcohols that are of use in the invention and commercially available are those sold by the company SEPPIC: Montanov™ 14 (INCI: Myristyl Alcohol & Myristyl Glucoside), Montanov™ 202 (INCI: Arachidyl Alcohol and Behenyl Alcohol and Arachidyl Glucoside), Montanov™ 68 (INCI: Cetearyl Alcohol & Cetearyl Glucoside), Montanov™ 82 (INCI: Cetearyl Alcohol and Coco-Glucoside), Montanov™ S (INCI: Coco-Glucoside & Coconut Alcohol), Montanov™ L (INCI: $C_{14}$-$C_{22}$ Alcohols & $C_{12}$-$C_{20}$ Alkyl Glucoside).

The preferred mixture of alkyl polyglucoside and fatty alcohol is that sold by SEPPIC under the name Montanov™ L, which is a mixture of $C_{14}$-$C_{22}$ fatty alcohols and of $C_{12}$-$C_{20}$ alkyl polyglucosides (INCI: $C_{14}$-$C_{22}$ Alcohols & $C_{12}$-$C_{20}$ Alkyl Glucoside). The more preferred mixture of alkyl polyglucoside and fatty alcohol is that sold by SEPPIC under the name Montanov™ 68 (INCI: Cetearyl Alcohol & Cetearyl Glucoside).

The O/W emulsifier of natural origin can also be selected from fatty esters of dextrins or of hydrolyzed starches, in particular in the form of sodium octenylsuccinate esters. These may, for example, be products marketed by the applicant under the names Cleargum® and in particular the products Cleargum® CO 01 and Cleargum® CO 03.

The emulsifying composition of the invention makes it possible to obtain advantageous sensorial effects, such as a particular texture or a sensation of freshness, according to the proportions used.

The advantageous properties of said emulsifying composition result from the combination of the two compounds used, which exhibit high synergy in terms of emulsion stability and of sensorial properties. Despite the highly satisfactory results obtained whatever the proportions in which these compounds are combined, the results obtained are particularly convincing when the compounds are combined in very specific ratio.

More particularly, each of the various constituents of the present emulsifying composition according to the invention may be integrated into a different phase prior to the emulsification. Alternatively, the various components of the present composition of the invention are mixed with one another to form what will hereinafter be denoted an "emulsifying system"; it being possible for said emulsifying system to be added to either of the two immiscible phases in order to allow the formation of an O/W emulsion. The invention, advantageously, allows these two embodiments with the same compounds, thereby providing increased room for maneuver and greater simplicity of use.

Such an emulsifying composition of the invention has the advantage, especially, of being entirely of natural origin, and of being utilizable by a cold process, and more particularly at ambient temperature. Said composition of the invention is for cosmetic use and, in that context, is not sensitive to reasonable variations in pH or in salinity of the medium, and is neither irritant nor liable to provoke allergies, especially skin allergies. Furthermore, the composition of the invention may be used for producing any type of emulsion, especially Pickering emulsions, and is therefore suitable for a wide variety of usages: creams, milks, serums, lotions, etc.

The emulsifying composition of the invention enables the production of Pickering emulsions, which advantageously may be stabilized by organic particles which are compatible with the skin or the hair. It may comprise, as a complement, other products which are capable of forming or stabilizing Pickering emulsions, such as silicas and granular octenylsuccinate starches in the form of calcium or aluminum salts.

The emulsifying composition preferably also comprises at least one polyol.

The polyols addressed for the present application are all the polyols otherwise known, and especially maltitol, mannitol, xylitol, erythritol, sorbitol, and glycerol, with glycerol and sorbitol being the preferred polyols. Preferably this polyol is crystallized or else is present in the form of a powder.

According to the present invention, the emulsifying composition, in particular for cosmetic use and capable of making it possible to obtain an emulsion of oil-in-water (O/W) type, contains, in % by weight:
1) from 40% to 95% of at least one cyclodextrin,
2) from 5% to 40% of at least one O/W emulsifier of natural origin, preferably selected from alkyl polyglucosides, mixtures of at least one alkyl polyglucoside and at least one fatty alcohol, and nonethoxylated fatty esters of polyols, having a hydrophilic-lipophilic balance (HLB) greater than 8, preferentially greater than or equal to 9,
3) and from 0% to 40% of at least one polyol.

This emulsifying composition of the present invention is preferably characterized in that it contains, in % by weight:
1) from 45% to 85% of at least one cyclodextrin,
2) from 5% to 30% of at least one O/W emulsifier of natural origin, preferably selected from alkyl polyglucosides, mixtures of at least one alkyl polyglucoside and at least one fatty alcohol, and nonethoxylated fatty esters of polyols, having a hydrophilic-lipophilic balance (HLB) greater than 8, preferentially greater than or equal to 9,
3) and from 10% to 40% of at least one polyol.

This composition of the present invention is most preferably characterized in that it contains, in % by weight:
1) from 40% to 80% of at least one cyclodextrin,
2) from 10% to 20% of at least one O/W emulsifier of natural origin, preferably selected from alkyl polyglucosides, mixtures of at least one alkyl polyglucoside and at least one fatty alcohol, and nonethoxylated fatty esters of polyols, having a hydrophilic-lipophilic balance (HLB) greater than 8, preferentially greater than or equal to 9,
3) and from 10% to 30% of at least one polyol.

Preferably, the O/W emulsifier of natural origin having a hydrophilic-lipophilic balance (HLB) greater than 8 is a product which is naturally biodegradable in a hydrated natural medium, and most preferentially a mixture of at least one alkyl polyglucoside and at least one fatty alcohol.

Another subject of the present invention relates to a Pickering O/W emulsion composition, in particular for cosmetic use, characterized in that it contains, per 1 part by weight of at least one cyclodextrin, between 0.01 and 1 part, preferably between 0.05 and 0.5 part, more preferentially between 0.10 and 0.35 part, and even better still between 0.15 and 0.30 part of at least one O/W emulsifier of natural origin, the latter preferably being selected from alkyl polyglucosides, mixtures of at least one alkyl polyglucoside and of at least one fatty alcohol, and nonethoxylated fatty esters of polyols, having a hydrophilic-lipophilic balance (HLB) greater than 8, preferentially greater than or equal to 9.

The O/W Pickering emulsion composition of the invention may also comprise a fatty phase which may, at ambient temperature (25° C.) be liquid, such as, for example, plant oils, or else solid as in the case of waxes. This liquid fatty phase may be mineral, animal, plant or synthetic in origin and may be composed of hydrocarbon-based oils or even possibly of silicone oils. A hydrocarbon-based oil is an oil formed essentially, or even consisting, of carbon and hydrogen atoms and optionally of oxygen and nitrogen atoms, it being possible for this oil to contain alcohol, ester, ether, carboxylic acid, amine and/or amide groups.

This composition preferably contains one or more oils which are liquid at ambient temperature (25° C.), preferably at least one nonvolatile liquid oil. A nonvolatile liquid oil refers to an oil capable of remaining on the skin at ambient temperature and atmospheric pressure for at least one hour.

The liquid fatty phase advantageously comprises one or more nonvolatile oils which impart an emollient effect on the skin. Mention may be made of fatty esters such as cetearyl isononanoate, isotridecyl isononanoate, isostearyl isostearate, isopropyl isostearate, isopropyl myristate, isopropyl palmitate, butyl stearate, hexyl laurate, isononyl isononanoate, 2-ethylhexyl palmitate, 2-hexyldecyl laurate, 2-octyldecyl palmitate, 2-octyldodecyl myristate or lactate, 2-diethylhexyl succinate, diisostearyl malate, tracetin, tricprin, caprylic/capric acid triglycerides, glycerol triisostearate, tocopherol acetate, higher fatty acids such as myristic acid, palmitic acid, stearic acid, behenic acid, oleic acid, linoleic acid, linolenic acid or isostearic acid, higher fatty alcohols such as oleyl alcohol, plant oils such as avocado oil, camelia oil, hazelnut oil, Tsubaki oil, cashew nut oil, argan oil, soybean oil, grapeseed oil, sesame oil, corn oil, wheatgerm oil, colza oil, sunflower oil, cotton oil, jojoba oil, peanut oil, olive oil, and mixtures thereof, plant butters such as karite butter and camelia butter.

These oils may be hydrocarbon oils or silicone oils, such as liquid paraffin, squalane oil, petroleum jelly, dimethylsiloxanes, and mixtures thereof.

The liquid fatty phase may also optionally comprise volatile oils. A volatile oil is an oil which is capable of evaporating from the skin in less than one hour at ambient temperature and atmospheric pressure. Volatile oils may, for example, be selected from silicone oils or triglycerides of short fatty acids, for reducing the greasy feel.

The O/W Pickering emulsion composition of the invention preferably contains only oils of renewable origin, and especially oils or butters of plant origin, preferably refined. These oils and butters are ideally in tune with the emulsifier system which is a subject of the invention, in the sense that they allow very stable emulsions to be obtained, with high whiteness and a readily adjustable viscosity.

The emulsifying composition of the invention advantageously allows the preparation of O/W emulsions having very high oil contents. This type of O/W emulsion rich in oil is commonly difficult to obtain in a form stable over time with conventional emulsifiers. The oil content of the final O/W emulsion is preferably between 10 and 65% by weight, and preferably of the order of 20 to 55% by weight. The plant oils or oils of plant origin such as, for example, sunflower oil and isopropyl palmitate have the more particular effect of allowing the production of stable emulsions, which do not give rise to creaming or to phase separation.

The composition of the invention may further comprise a rheological agent such as, especially, a thickening agent for the aqueous phase, a gelling agent or a suspension agent, such as, for example, gums obtained from plants, such as gum Arabic, konjac gum, guar gum or derivatives thereof; gums extracted from algae such as alginates or carrageenans; gums obtained from microbial fermentation such as xanthans, mannans, scleroglucans, or derivatives thereof; cellulose and its derivatives, such as carboxymethylcellulose or hydroxyethylcellulose; starch and its derivatives such as, more particularly, modified starches, especially acetylated, carboxymethylated, octenylsuccinate or hydroxypropylated starches; and synthetic polymers such as polyacrylic acids or carbomers.

The composition of the invention preferably comprises a rheological agent selected from natural polysaccharides obtained from plants or from fermentation, which are optionally modified. Xanthan and derivatives thereof make it possible more particularly to obtain O/W emulsions having very fine droplet sizes, even when used in a content of less than 1% by weight of the total emulsion.

The emulsions obtained by using the emulsifying composition according to the invention preferably have a droplet size of less than or equal to 30 µm, preferentially less than or equal to 10 µm. The term "droplet size of the emulsion" is intended to mean the mean diameter of the droplets of dispersed fatty phase in suspension in the aqueous phase. A low droplet size increases the stability of the emulsion by reducing the rate of flocculation of the emulsion, and hence the rate of phase separation. The droplet size is dependent on a large number of parameters and, in this respect, represents a feature which it is appropriate to monitor and which is not intrinsic to the formulation of the emulsifying system. The droplet size is measured using a LEICA DMLS optical microscope at ×10 magnification.

The composition of the invention may further comprise a preservative selected from benzyl alcohol, dehydroacetic acid, and mixtures thereof.

The composition of the invention preferably has a Brookfield viscosity of greater than 3000 mPas at 25° C., preferably greater than 5000 mPas at 25° C. The viscosity is measured using a Brookfield DV-II+Pro viscometer which is rotated at a speed of 20 revolutions per minute in contact with the product sample. The resistance of the product to this rotary movement is recorded for a minute and converted into mPascal-second. For each sample, the viscosity is measured three times and the arithmetic mean of the three values is retained. A spindle suitable for the measured viscosity is selected according to the following ranges: the spindle selected is the spindle SP3 when the viscosity is less than or equal to 5000 mPa·s, SP4 when the viscosity is between 5000 mPa·s and 7000 mPa·s and SP5 when the viscosity is greater than or equal to 7000 mPa·s.

To characterize the sensorial properties of the emulsifier systems of the invention, use is made of sensorial descriptors and a corresponding 5-step sensorial evaluation protocol. These 5 steps correspond to the various phases of application of a care product: appearance, pickup, spreading after 1 minute, after 2 minutes. During these 5 phases, a number of sensorial descriptors are evaluated by a panel of evaluators, who award a score which may range from 0 to 10.

The composition of the invention preferably exhibits a whiteness descriptor of greater than 8. The whiteness descriptor is defined by the palette of colors in FIG. 1. The product is examined under a lamp and compared with the color palette by a panel of evaluators.

The composition of the invention preferably exhibits a brightness descriptor of greater than or equal to 8. The brightness is defined by the propensity of the product to reflect light.

The composition of the invention preferably exhibits a spreading descriptor of greater than 8. The spreading is evaluated by examining the product after the placement on the hand of 50 to 100 μl of the product, during its spreading in 10 rotations, under a lamp. The less the resistance to movement between the 5th and 10th turn on the hand, the greater the spreading.

The composition of the invention preferably exhibits a film-forming descriptor of greater than 8. The film-forming descriptor corresponds to the propensity of the product to form a continuous film when slid over the skin 2 minutes after having performed 10 rotations.

A further subject of the present invention is a process for producing an O/W Pickering emulsion composition, especially for cosmetic use, which comprises the following steps:
  a) the dispersion in an aqueous phase of an emulsifying composition comprising at least one cyclodextrin and at least one O/W emulsifier of natural origin, the latter being present in a ratio of between 0.01 and 1 part, preferably between 0.05 and 0.5 part, more preferentially between 0.10 and 0.35 part, and even better still between 0.15 and 0.30 part, per 1 part by weight of at least this cyclodextrin; it being possible for this O/W emulsifier of natural origin to be selected in particular from at least one alkyl polyglucoside, at least one mixture of at least one alkyl polyglucoside and at least one fatty alcohol, and at least one nonethoxylated fatty ester of polyols, more preferentially selected from mixtures of at least one alkyl polyglucoside and of at least one fatty alcohol, having a hydrophilic-lipophilic balance (HLB) of less than 8, preferentially greater than or equal to 9,
  b) the addition, to the mixture obtained in step a), of a fatty phase, preferably in an amount of between 10 and 65% by weight, and preferably of about 20 to 55% by weight, relative to the final weight of the emulsion, with mechanical stirring sufficient to allow the fatty phase to be dispersed as fine droplets in the aqueous phase and for an O/W emulsion which has a droplet size of less than or equal to 30 μm, preferentially less than or equal to 10 μm, to be obtained.

According to one variant, the process of the invention for producing an O/W Pickering emulsion composition, especially for cosmetic use, comprises the following steps:
  a) the dispersion in a fatty phase of an emulsifying composition comprising at least one cyclodextrin and at least one O/W emulsifier of natural origin, the latter being present in a ratio of between 0.01 and 1 part, preferably between 0.05 and 0.5 part, more preferentially between 0.10 and 0.35 part, and even better still between 0.15 and 0.30 part, per 1 part by weight of at least this cyclodextrin; it being possible for this O/W emulsifier of natural origin to be selected in particular from at least one alkyl polyglucoside, a mixture of at least one alkyl polyglucoside and at least one fatty alcohol, and a nonethoxylated fatty ester of polyols, more preferentially selected from mixtures of at least one alkyl polyglucoside and of at least one fatty alcohol, having a hydrophilic-lipophilic balance (HLB) of greater than 8, preferentially greater than or equal to 9;
  the fatty phase preferentially representing between 10 and 65% by weight, and preferably about 20 to 55% by weight, of the final weight of the emulsion,
  b) and the addition of the mixture obtained in step a) to an aqueous phase, with mechanical stirring sufficient to allow the fatty phase to be dispersed as fine droplets in the aqueous phase and for an O/W emulsion which has a droplet size of less than or equal to 30 μm, preferentially less than or equal to 10 μm, to be obtained.

It will be possible to understand the invention more clearly by means of the nonlimiting exemplary embodiments described below.

EXAMPLE 1

It will be possible to understand the invention more clearly by means of the nonlimiting exemplary embodiments described below, and by examination of the appended figures.

Six compositions in O/W emulsion form are produced according to the invention, using the following protocol. The compositions of these 6 compositions are reported in table 1.

To start with, a gelling agent is dispersed in water, with stirring using a deflocculating blade at 1000 revolutions per minute. The temperature of the water is set at 40° C. when the gelling agent is xanthan gum, and at 70° C. when the gelling agent is hydroxyethylcellulose.

Beta-cyclodextrin is then wetted in glycerol, and the beta-cyclodextrin/glycerol mixture is added to the water/gelling agent mixture with stirring at 1000 revolutions per minute, to give an aqueous phase.

The amount of beta cyclodextrins is set at 2% or at 5% by mass of the composition, depending on the cases.

Separately, the alkyl polyglucoside Montanov 68 (INCI: cetearyl alcohol & cetearyl glucose), from the company SEPPIC, is added to sunflower oil or to isopropyl palmitate with magnetic stirring, at 40° C., to obtain an oily phase.

The oily phase is then emulsified in the aqueous phase at 40° C. with stirring at 1500 revolutions per minute, for 15 minutes.

A preservative is added (mixture based on benzyl alcohol and dehydroacetic acid).

TABLE 1

| | % Beta-cyclodextrin | Oil (30%) | Emulsifier (1%) | Thickener (0.7%) |
|---|---|---|---|---|
| 1 | 5 | Sunflower | Montanov ™ 68 | Hydroxyethylcellulose |
| 2 | 5 | Sunflower | Montanov ™ 68 | Hydroxyethylcellulose |
| 3 | 2 | Isopropyl Palmitate (IPP) | Montanov ™ 68 | Hydroxyethylcellulose |
| 4 | 2 | Sunflower | Montanov ™ 68 | Xanthan |
| 5 | 2 | Isopropyl Palmitate (IPP) | Montanov ™ 68 | Xanthan |
| 6 | 5 | Isopropyl Palmitate (IPP) | Montanov ™ 68 | Xanthan |

Figure 2:
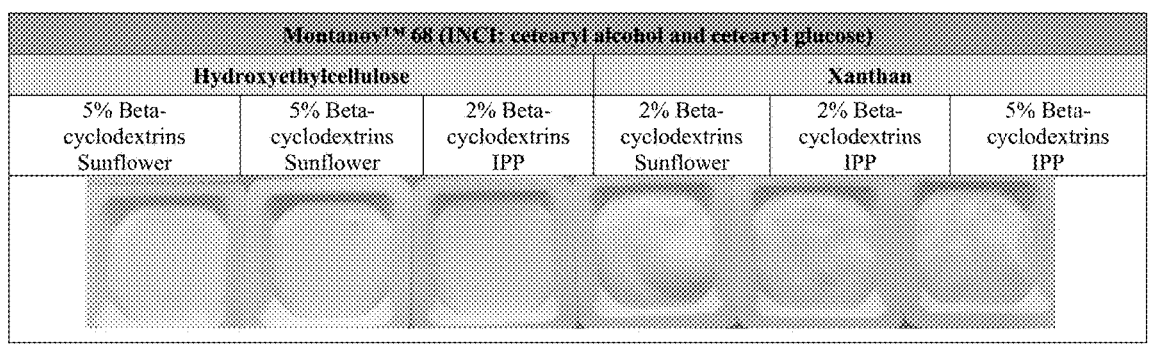
FIG. 2 is a photograph of 6 O/W emulsions obtained from emulsifying compositions of the invention.

FIG. 2 is a photograph of the 6 O/W emulsions obtained, according to the formulations given in table 1.

It is noted that all the emulsions according to the invention comprising 1% of Montanov™ 68 (cetearyl alcohol and cetearyl glucose) and 2 or 5% of beta-cyclodextrin make it possible to obtain stable O/W emulsions, using only 1 wt % of customary O/W emulsifier.

For each of these compositions, measurements are made of the viscosity, droplet size, whiteness, spreading, greasy character, and penetrative character. The compositions will be designated indiscriminately using the terms samples or product in the remainder of the present detailed description.

The viscosity is measured using a Brookfield DV-II+Pro viscometer. A spindle of fixed size (spindles SP2 to SP7, used according to the viscosity levels in accordance with the instrument setpoints) is rotated at a speed of 20 revolutions per minute in contact with the product sample. The resistance of the product to this rotational movement is recorded for one minute and converted into mPascal-second, denoted mPa·s. For each sample, the viscosity is measured three times and the arithmetic mean of the three values is retained.

Figure 1:
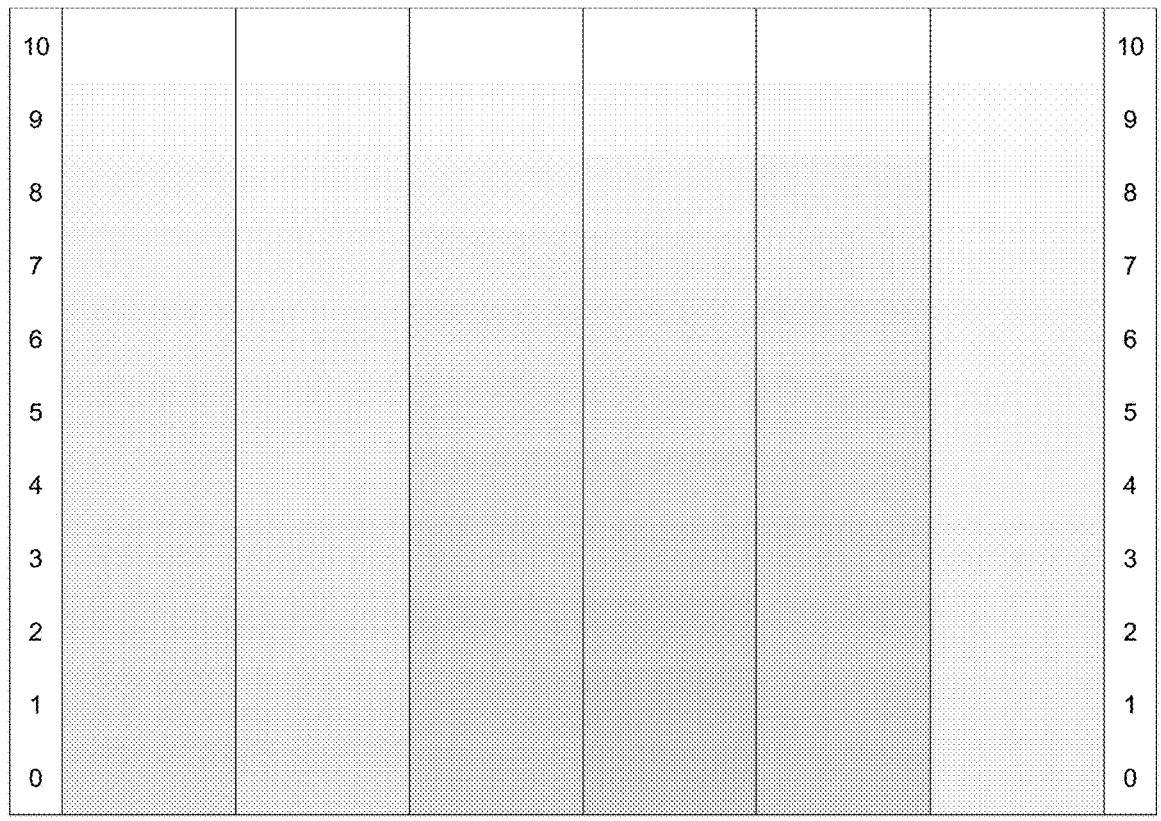
FIG. 1 represents the range of colors used for evaluating the whiteness descriptor.

The whiteness descriptor is defined by the palette of colors in FIG. 1. The product is examined under a lamp and compared with the color palette by a panel of evaluators.

The spreading is evaluated by examining the product after the placement on the hand of 50 to 100 μl of the product, during its spreading in 10 rotations, under a lamp. The less the resistance to movement between the $5^{th}$ and $10^{th}$ turn on the hand, the greater the spreading.

The greasy character of the compositions is evaluated by examination under a lamp of product, 1 minute after having performed 10 rotations of the product on the skin. A panel of evaluators then evaluates the resistance of the product when the skin to which it has been applied is placed between the thumb and the index finger and a rubbing movement is applied. The panel of evaluators also takes account of the oily or nonoily appearance imparted to the skin.

Lastly, the penetrative character of the product is evaluated by examination under a lamp of the product two minutes after having performed 10 rotations of the product on the skin, by carrying out sliding over the skin. A panel of evaluators then evaluates the amount of product residue recovered.

The results obtained for the 6 O/W emulsion compositions are set out in table 2.

TABLE 2

| | Viscosity in mPa · s (spindle used) | Droplet size (microns) | White | Spreading | Greasiness | Penetration |
|---|---|---|---|---|---|---|
| 1 | 12 120 (SP5) | Less than 10 | 10 | 7 | 7 | 10 |
| 2 | 12 233 (SP5) | Less than 10 | 10 | 7 | 7 | 10 |
| 3 | 4417 (SP3) | Less than 10 | 10 | 8 | 5 | 10 |
| 4 | 4917 (SP3) | From 10 to 30 | 9 | 10 | 7 | 8 |
| 5 | 3940 (SP3) | From 10 to 20 | 10 | 10 | 6 | 10 |
| 6 | 4517 (SP3) | From 10 to 30 | 9 | 10 | 9 | 7 |

The viscosity of the emulsions increases slightly when the concentration of beta-cyclodextrin increases: it goes from 3900-4900 mPa·s with 2% of beta-cyclodextrin to more than 12 000 mPas with 5%. Similarly, the viscosity is higher when the thickener used is cellulose rather than xanthan: it goes from 4500 to 12 000 mPa·s. The emulsifying compositions of the invention enable the realization, advantageously, of a very wide viscosity range, allowing the preparation both of milks and of viscous creams.

It may be noted that all of the O/W emulsions obtained using the emulsifying compositions of the invention exhibit excellent sensorial properties (scores ranging from 6 to 10 according to the criteria of whiteness, spreading, greasiness, and penetration).

The emulsions are less white when the oil used is sunflower oil than when the oil used is isopropyl palmitate (denoted IPP): the descriptor is 10 out of 10 in the case of the sunflower oil, compared to 9.33 out of 10 on average in the case of isopropyl palmitate. However, the whiteness of isopropyl palmitate remains satisfactory.

The spreading is significantly easier with xanthan than with cellulose, and goes from 7.33 with cellulose to 10 with xanthan.

The invention claimed is:

1. An emulsifying composition, for cosmetic use, allowing an oil-in-water (O/W) emulsion to be obtained, the emulsifying composition comprising consisting of:
    a. at least one cyclodextrin, and
    b. at least one O/W emulsifier, wherein the least one O/W emulsifier is a mixture of at least one $C_{12}$-$C_{20}$ alkyl polyglucoside and at least one linear or branched fatty alcohol having a total carbon atom number ranging from 8 to 24,
    c. optionally at least one polyol;
    the at least one O/W emulsifier having a hydrophilic-lipophilic balance (HLB) greater than 8.

2. The emulsifying composition as claimed in claim 1, characterized in that the at least one O/W emulsifier is present in the emulsifying composition in a ratio of between 0.01 and 1 part, per 1 part by weight of the at least one cyclodextrin.

3. The emulsifying composition as claimed in claim 1, wherein said at least one cyclodextrin is selected from alpha-, beta-, and gamma-cyclodextrins.

4. The emulsifying composition as claimed in claim 1, wherein the at least one cyclodextrin is present in the form of a crystalline, pseudo-crystalline or amorphous powder.

5. The emulsifying composition as claimed in claim 1, wherein the at least one O/W emulsifier is products which are naturally biodegradable in a hydrated natural medium with a hydrophilic-lipophilic balance (HLB) of between 8 and 20.

6. The emulsifying composition as claimed in claim 1, wherein the at least one O/W emulsifier is a mixture consisting of $C_{14}$-$C_{22}$ fatty alcohol and of $C_{12}$-$C_{20}$ alkyl polyglucoside.

7. The emulsifying composition as claimed in claim 1, wherein the at least one polyol is selected from maltitol, mannitol, xylitol, erythritol, sorbitol and glycerol.

8. The emulsifying composition as claimed in claim 1, wherein the composition consists, in % by weight:
    a. 40% to 95% of the at least one cyclodextrin,
    b. 5% to 40% of the mixture of at least one $C_{12}$-$C_{20}$ alkyl polyglucoside and at least one linear or branched fatty alcohol having a total number of carbon atoms ranging from 8 to 24, having a hydrophilic-lipophilic balance (HLB) greater than 8, and
    c. 0% to 40% of the at least one polyol.

9. An emulsifying composition as claimed in claim 1 wherein the at least one O/W emulsifier has a hydrophilic balance (HLB) greater than or equal to 9.

10. The emulsifying composition as claimed in claim 1, characterized in that the at least one O/W emulsifier is present in the emulsifying composition in a ratio of between 0.05 and 0.5 part per 1 part by weight of the at least one cyclodextrin.

11. The emulsifying composition as claimed in claim 1, characterized in that the at least one O/W emulsifier is present in the emulsifying composition in a ratio of between 0.10 and 0.35 part per 1 part by weight of the at least one cyclodextrin.

12. The emulsifying composition as claimed in claim 1, characterized in that the at least one O/W emulsifier is present in the emulsifying composition in a ratio of between 0.15 and 0.30 part per 1 part by weight of the at least one cyclodextrin.

13. The emulsifying composition as claimed in claim 1, wherein said at least one cyclodextrin is a native beta-cyclodextrin.

14. The emulsifying composition as claimed in claim 1, wherein the at least one O/W emulsifier is products which are naturally biodegradable in a hydrated natural medium with a hydrophilic-lipophilic balance (HLB) of between 9 and 16.

15. The emulsifying composition as claimed in claim 1, wherein the composition consists of,
    (a) the at least one cyclodextrin,
    (b) 5% to 40%, in % by weight, of the mixture of at least one $C_{12}$-$C_{20}$ alkyl polyglucoside and at least one linear or branched fatty alcohol having a total number of carbon atoms ranging from 8 to 24, having a hydrophilic-lipophilic balance (HLB) greater than or equal to 9, and
    (c) optionally the at least one polyol.

* * * * *